US007256259B2

(12) United States Patent
Raines et al.

(10) Patent No.: US 7,256,259 B2
(45) Date of Patent: *Aug. 14, 2007

(54) METHODS FOR LIGATION OF MOLECULES TO SURFACES

(75) Inventors: Ronald T. Raines, Madison, WI (US); Matthew B. Soellner, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 181 days.

This patent is subject to a terminal disclaimer.

(21) Appl. No.: 10/930,702

(22) Filed: Aug. 30, 2004

(65) Prior Publication Data

US 2005/0048192 A1    Mar. 3, 2005

Related U.S. Application Data

(63) Continuation-in-part of application No. 10/276,515, filed as application No. PCT/US01/15440 on May 11, 2001, now Pat. No. 6,972,320.

(60) Provisional application No. 60/499,231, filed on Aug. 29, 2003, provisional application No. 60/203,994, filed on May 12, 2000.

(51) Int. Cl.
| B05D 3/10 | (2006.01) |
| C07K 1/04 | (2006.01) |
| C07K 17/00 | (2006.01) |
| C23C 22/00 | (2006.01) |
| H01L 21/02 | (2006.01) |

(52) U.S. Cl. .................. 530/345; 148/250; 427/337; 427/338; 438/765; 530/402; 530/810

(58) Field of Classification Search ................ None
See application file for complete search history.

(56) References Cited

U.S. PATENT DOCUMENTS

| 4,066,684 | A | 1/1978 | Dorman et al. ............ 260/112.5 |
| 5,300,278 | A | 4/1994 | Pasqualini et al. .............. 534/14 |
| 5,541,289 | A | 7/1996 | Gilbertson .................. 530/327 |
| 5,543,389 | A | 8/1996 | Yatvin et al. ................... 514/2 |
| 6,570,040 | B2 | 5/2003 | Saxon et al. ................. 568/17 |
| 6,972,320 | B2 * | 12/2005 | Raines et al. ............... 530/339 |
| 2002/0016003 | A1 | 2/2002 | Saxon et al. ................. 435/441 |
| 2003/0199084 | A1 | 10/2003 | Saxon et al. ................. 435/325 |

FOREIGN PATENT DOCUMENTS

| WO | WO 01/68565 | 9/2001 |
| WO | WO 01/87920 | * 11/2001 |

OTHER PUBLICATIONS

Afonso, C. A. M. (1998), "Studies on the Transformation of Azido-Group to N-(t-Butoxycarbonyl)amino group via Staudinger Reaction," *Synthetic Commun.*, 28:261-276.

Ariza X. et al. (1998), "One-Pot Conversion of Azides to Boc-Protected Amines with Trimethylphosphine and Boc-ON," *Tetrahedron Lett.* 39:9101-9102.
Ariza, X. et al. (Jul. 2001), "From vacinal azido alcohols to boc-amino alcohols or oxazolidonones, with trimethylphosphine and $Boc_2O$ or $CO_2$," Tetrahedron Lett. 42:4995-4999.
Ayers, B. et al. (Feb. 1999), "Introduction of Unnatural Amino Acids into Proteins Using Expressed Protein Ligation," *Biopolymers* (including Peptide Science) 51:343-354 (published on-line Feb. 2000).
Backes, B. J.; Ellman, J. A. (Mar. 1999), "An Alkanesulfonamide 'Safety-Catch' Linker for Solid-Phase Synthesis," *J. Org. Chem.* 64: 2322-2330.
Block, E. et al. (1989), "2-Phosphino- and 2-Phosphinylbenzenethiols: New Ligand Types," *J. Am. Chem. Soc.* 111: 2327-2329.
Borgia, J.A..; Fields, G.B. (Jun. 2000), "Chemical synthesis of proteins," *Trends Biotechnol.* 18: 243-251.
Bosch, I. et al. (1993), "Alternative Procedures for the Macrolactamisation of ω-Azido Acids," *Tetrahedron Lett.* 34:4671-4674.
Bosch, I. et al. (1995), "Epimerisation-free Peptide Formation from Carboxylic Acid Anhydrides and Azido Derivatives," *J. Chem. Soc., Chem. Commun.* pp. 91-92.
Bosch, I. et al. (1996), "On the Reaction of Acyl Chlorides and Carboxylic Anhydrides with Phosphazenes," *J. Org. Chem.* 61:5638-5643.
Boullanger P. et al. (Feb. 2000), "Syntheses of amphiphilic glycosylamides from glycosyl azides without transient reduction to glycosylamines," *Carbohydr. Res.* 324:97-106
Brik, A. et al. (Jun. 2000), "Protein Synthesis by Solid-Phase Chemical Ligation Using a Safety Catch Linker," *J. Org. Chem.* 65(12): 3829-3835.
Brisset, H. et al. (1993), "Phosphine-Borane Complexes; Direct Usein Asymmetric Catalysis," Tetrahedron Lett. 34:4523-4526.
Bruice, T. C.; Pandit, U. K. (1960), "The Effect of Geminal Substitution Ring Size and Rotamer Distribution on the Intramolecular Nucleophilic Catalysis of the Hydrolysis of Monophenyl Esters of Dibasic Acids and the Solvolysis of the Intermediate Anhydrides," *J. Am. Chem. Soc.* 82:5858-5865.
Brunel, J.M. et al. (1998), "Phosphane-boranes: synthesis, characterization and synthetic applications," Coord. Chem. Rev. 180:665-698.
Cane, D.E. et al. (1998), "Harnessing the Biosynthetic Code: Combinations, Permutations, and Mutations," *Science* 282:63-68.
Carboni, B. and Monnier, L. (Jan. 1999), "Recent Developments in the Chemistry of Amine- and Phosphine-Boranes," Tetrahedron 55:1197-1248.
Charrier, C.; Mathey, F. (1978), "La Diphenyl-Cyclopentadienylmethyl-Phosphine FT SFS Complexes," (in French) *Tetrahedron Lett.* 27:2407-2410. .

(Continued)

*Primary Examiner*—Jeffrey Edwin Russel
(74) *Attorney, Agent, or Firm*—Greenlee, Winner and Sullivan, P.C.

(57) ABSTRACT

The present invention is a method for a covalent ligation of one or more molecules to one or more surfaces, that is site-specific and both rapid and high yielding. The covalent ligation to the surface is based on the reaction of an azide and a phosphinothioester to form an amide bond. The method of the invention is particularly well-suited to the immobilization of peptides, proteins or protein fragments to surfaces.

22 Claims, 1 Drawing Sheet

OTHER PUBLICATIONS

Cotton, G. J.; Muir, T. W. (Sep. 1999), "Peptide ligation and its application to protein engineering," *Chem. Biol.* 6: R247-R256.

Dawson, P. E. et al. (1994), "Synthesis of Proteins by Native Chemical Ligation," *Science* 266: 776-779.

Dawson, P.E.; Kent, S.B.H. (Jul. 2000), "Synthesis of Native Proteins by Chemical Ligation," *Annu. Rev. Biochem.* 69:923-960.

Dawson, P. E. et al. (1997), "Modulation of Reactivity in Native Chemical Ligation through the Use of Thiol Additives," *J. Am. Chem. Soc.* 119: 4325-4329.

Drijfhout et al. (Dec. 2000), Chemical Abstracts (Columbus, Ohio, USA) No. 133:135556. Abstract of "Methods of Preparing Peptide-Carrier Conjugates," in *Fmoc Solid Phase Peptide Synthesis*), pp. 229-241.

Evans, Jr., T. C. et al. (1998), "Semisynthesis of cytotoxic proteins using a modified protein splicing element," *Protein Sci.* 7:2256-2264.

Evans, Jr., T. C.; Xu, M. -Q. (pub. on-line Feb. 2000), "Intein-Mediated Protein Ligation: Harnessing Nature's Escape Artists," *Biopolymers* 51:333-342.

Farrington, G.K. et al. (1989), "A Convenient Synthesis of Diethyl (Mercaptomethyl)Phosphonate," *Org. Prep. Proced. Int.* 21:390-392.

Friedman, M. (Apr. 1999), "Lysinoalanine in Food and in Antimicrobial Proteins," *Adv. Exp. Med. Biol.* 459:145-159.

Garcia, J. et al. (1984), "New Synthetic "Tricks." Triphenylphosphine-Mediated Amide Formation from Carboxylic Acids and Azides," *Tetrahedron Lett.* 25:4841-4844.

Garcia, J.; Vilarrasa, J. (1986), "New Synthetic "Tricks." One-pot Preparation of N-Substituted Phthalimides from Azides and Phthalic Anhydride," *Tetrahedron Lett.* 27:639-640.

Gilbertson, S. (Aug. 2001), "High-Yielding Staudinger Ligation of Phosphinoesters and Azides to Form Amides," *Chemtracts-Org. Chem.* 14:524-528.

Gololobov, Yu. G.; Kasukhin, L. F. (1992), "Recent Advances in the Staudinger Reaction," *Tetrahedron* 48: 1353-1406.

Gololobov, Yu. G. et al. (1981), "Sixty Years of Staudinger Reaction," *Tetrahedron* 37: 437-472.

Holford, M.; Muir, T. W. (1998), "Adding 'splice' to protein engineering," *Structure* 15: 951-956.

Imamoto, T. et al. (1990), "Synthesis and Reactions of Phosphine-Boranes. Synthesis of New Bidentate Ligands with Homochiral Phosphine Centers via Optically Pure Phosphine-Boranes," *J. Am. Chem. Soc.* 112:5244-5252.

Inazu, T.; Kobayashi, K. (1993), "A New Simple Method for the Synthesis of $N^\alpha$-Fmoc-$N^\beta$-Glycosylated-L-Asparagine Derivative," *Synlett.* pp. 869-870.

Ingenito, R. et al. (Nov. 1999), "Solid Phase Synthesis of Peptide C-Terminal Thioesters by Fmoc/*t*-Bu Chemistry," *J. Am. Chem. Soc.* 121:11369-11374.

Janssen, M. J. *The Chemistry of Carboxylic Acids and Esters*; Patai, S., Ed.; Interscience Publishers: New York, 1969; pp. 730-736.

Jung, M. E.; Gervay, J. (1991), "gem-Dialkyl Effect in the Intramolecular Diels-Alder Reaction of 2-Furfuryl Methyl Fumarates: The Reactive Rotamer Effect, Enthalpic Basis for Acceleration, and Evidence for a Polar Transition State," *J. Am. Chem. Soc.* 113: 224-232.

Kaiser, E. T. (1989), "Synthetic Approaches to Biologically Active Peptides and Proteins Including Enzymes," *Acc. Chem. Res.* 22:47-54.

Katz, L. (1997), "Manipulation of Modular Polyketide Synthases," *Chem. Rev.* 97:2557-2575.

Keating, T.A; Walsch, C.T. (Oct. 1999), "Initiation, elongation, and termination strategies in polyketide and polypeptide antibiotic biosynthesis," *Curr. Opin. Chem. Biol.* 3:598-606.

Kemp, D. S.; Galakatos, N. G. (1986), "Peptide Synthesis by Prior Thiol Capture. 1. A Convenient Synthesis of 4-Hydroxy-6-mercaptodibenzofuran and Novel Solid-Phase Synthesis of Peptide-Derived 4-(Acyloxy)-6-mercaptodibenzofurans," *J. Org. Chem.* 51:1821-1829.

Kent, S. B. (1988), "Chemical Synthesis of Peptides and Proteins," *Annu. Rev. Biochem.* 57: 957-989.

Khosla, C. (1997), "Harnessing the Biosynthetic Potential of Modular Polyketide Synthases," *Chem. Rev.* 97:2577-2590.

Kiick, K.L. et al. (Jan. 2002), "Incorporation of azides into recombinant proteins for chemoselective modification by the Staudinger ligation," *Proc. Natl. Acad. Sci. USA* 99:19-24.

Kochendoerfer, G. G.; Kent, S. B. H. (Dec. 1999), "Chemical protein synthesis," *Curr. Opin. Chem. Biol.* 3:665-671.

Konz, D.; Marahiel, M.A. (Feb. 1999), "How do peptide synthetases generate structural diversity?" *Chem. Biol*6: R39-R48.

Lamoureux, G. V.; Whitesides, G. M. (1993), "Synthesis of Dithiols as Reducing Agents for Disulfides in Neutral Aqueous Solution and Comparison of Reduction Potentials," *J. Org. Chem.* 58:633-641.

Leffler et al. (1967) "The Staudinger Reaction between Triarylphosphines and Azides. A Study of the Mechanism," *J. Am. Chem. Soc.* 89:5235-5246.

Lemieux et al. (1998), "Chemoselective ligation reactions with proteins, oligosaccharides and cells," *Trends Biotechnol.* 16:506-513.

Lemieux G.A. et al. (Apr. 2003), "A fluorogenic dye activated by the staudinger ligation," *J. Am. Chem. Soc.* 125:4708-4709.

Lu, W. et al. (1996), "Comparative Total Syntheses of Turkey Ovomucoid Third Domain by Both Stepwise Solid Phase Peptide Synthesis and Native Chemical Ligation," *J. Am. Chem. Soc.* 118:8518-8623.

Lundberg et al. (1969) Chemical Abstracts (Columbus, Ohio, USA) No. 71:18411.

Abstract of Inorganic Chemistry (1969) 8(6): 1336-1340.

Lundquist, J.T., IV. and Pelletier, J.C. (Mar. 2001), "Improved Solid-Phase Peptide Synthesis Method Utilizing α-azide-Protected Amino Acids," *Org. Lett.* 3:781-783.

Malkinson, J. P. et al. (Aug. 2000), "Synthesis of C-Terminal Glycopeptides from Resin-Bound Glycosyl Azides via a Modified Staudinger Reaction," *J. Org. Chem.* 65: 5249-5252.

Marahiel, M.A. et al. (1997), "Modular Peptide Synthetases Involved in Nonribosomal Peptide Synthesis," *Chem. Rev.* 97:2651-2673.

Marcaurelle et al. (1998), "Direct Incorporation of Unprotected Ketone Groups into Peptides During Solid-Phase Synthesis: Application to the One-Step Modification of Peptides with Two Different Biophysical Probes for FRET," Tetrahedron Lett. 39:7279-7282.

Maunier, V. et al. (1997), "Synthesis and surface-active properties of amphiphilic 6-aminocarbonyl derivatives of D-glucose," *Carbohydr. Res.* 299:49-57.

Maunier, V. et al. (1997), "A One-Pot Synthesis of Glycosyl Amides from Glycosyl Azides Using a Modified Staudinger Reaction," J. Carbohydrate Chem. 16:231-235.

McCaldon, P.; Argos, P. (1988), "Oligopeptide Biases in Protein Sequences and Their Use in Predicting Protein Coding Regions in Nucleotide Sequences," *Proteins* 4: 99-122.

Meldal, M. et al. (1997), "Azido Acids in a Novel Method of Solid-Phase Peptide Synthesis," *Tetrahedron Lett.* 38:2531-2534.

Merrifield, R. B. (1984), "Solid Phase Synthesis," *Science* 232: 341-347.

Miranda, L.P. and Alewood, P.F. (pub. on-line Nov. 2000), "Challenges for Protein Chemical Synthesis in the 21st Century: Bridging Genomics and Proteomics," *Biopolymers* 55:217-226.

Mizuno, M. et al. (Jan. 1999), "A Simple Method for the Synthesis of $N^\beta$-Glycosylated-Asparagine and -Glutamine Derivatives," *Synthesis-Stuttgart*, pp. 162-165.

Mizuno, M. et al. (Jan. 1999), "Synthesis of a Glycopeptide Containing Oligosaccharides: Chemoenzymatic Synthesis of Eel Calcitonin Analogues Having Natural N-Linked Oligosaccharides," *J. Am. Chem. Soc.* 121:284-290.

Molina, P.; Vilaplana, M. J. (1994), "Iminophosphoranes: Useful Building Blocks for the Preparation of Nitrogen-Containing Heterocycles," *Synthesis-Stuttgart* pp. 1197-1218.

Muir, T. W. et al. (1997), "Protein Synthesis by Chemical Ligation of Unprotected Peptides in Aqueous Solution," *Methods Enzymol.* 289: 266-298.

Muir, T. W. et al. (1998), "Expressed protein ligation: A general method for protein engineering," *Proc. Natl. Acad. Sci. U.S.A.* 9:6705-6710.

Nilsson, B.L. et al. (Jun. 2000), "Staudinger Ligation: A Peptide from a Thioester and Azide," *Org. Lett.* 2:1939-1941.

Nilsson, B.L. et al. (pub. on-line Dec. 2000), "High-Yielding Staudinger Ligation of a Phosphinothioester and Azide to Form a Peptide," Org. Lett. 3:9-12.

Nilsson, B.L. et al. (2000), "Staudinger Ligation: A Peptide from a Thioester and Azide," 2:1939-1941 Org. Lett.

Nilsson, B.L. et al. (May 2003), "Protein assembly by orthogonal chemical ligation methods," J. Am. Chem. Soc. 125:5268-5269.

Offer, J.; Dawson, P. E. (Jan. 2000), "$N^\alpha$-2-Mercaptobenzylamine-Assisted Chemical Ligation," *Org. Lett.* 2:23-26.

Patel, et al. (1995), Chemical Abstracts (Columbus, Ohio, USA) No. 122:133805. Abstract of J. Med. Chem. (1995) 38(3):435-442.

Perez-Lourido, P. et al. (Jan. 2000), "Diorganotin (IV) derivatives of arenephosphinothiol ligands. The crystal structure of [$Ph_2Sn$(2-($Ph_2P$)$C_6H_4S$)$_2$] and [$Me_2Sn${2-($Ph_2PO$)-6-($Me_3Si$)$C_6H_3S$}$_2$],I" J. Organomet. Chem. 595:59-65.

Perich, J.W.; and Johns, RB (1988), "Di-*tert*-butyl *N,N*-Diethylphosphoramidite. A New Phosphitylating Agent for the Efficient Phosphorylation of Alcohols," Synthesis-Stuttgart 2:142-144.

Raines, R. T. (1997), "Nature's transitory covalent bond," *Nature Struct. Biol. 4*: 424-427.

Ravindar et al. (1992), "A Novel Convenient Synthesis of Aryl Phosphines Containing Reactive Functional Groups," Synth. Comm. 22:1453-1459.

Reist, M. et al. (1995), "Racemization, Enantiomerization, Diastereomerization, and Epimerization—Their Meaning and Pharmacological Significance," Chirality 7:396-400 (Abstract only).

Romoff, T.T. and Goodman, M. (1997), "Urethane-protected N-Carboxyanhydrides (UNCAs) as unique reactants for the study of intrinsic racemization tendencies in peptide synthesis," J. Peptide Res. 49:281-292.

Saxon, E.; Bertozzi, C. R. (Mar. 2000), "Cell Surface Engineering by a Modified Staudinger Reaction," Science 287:2007-2010.

Saxon et al. (Aug. 1999), "Development of a New Chemoselective Ligation Reaction," Abstracts of Papers American Chemical Society 218: (1-2), pp. Carb 23.

Saxon, E. et al. (Jun. 2000), "A 'Traceless' Staudinger Ligation for the Chemoselective Synthesis of Amide Bonds," *Org. Lett.* 2:2141-2143.

Schneider, C. H.; de Weck, A. L. (1965), "Studies on the Direct Neutral Penicilloylation of Functional Groups Occurring on Proteins," *Biochim. Biophys. Acta 168*:27-35.

Shalev, D. E. et al. (1996), "Sequence of Reactant Combination Alters the Course of the Staudinger Reaction of Azides with Acyl Derivatives. Bimanes. 30," *J. Org. Chem.* 61:1689-1701.

Shin, Y. et al. (Dec. 1999), "Fmoc-Based Synthesis of Peptide-αThioesters: Application to the Total Chemical Synthesis of a Glycoprotein by Native Chemical Ligation," *J. Am. Chem. Soc.* 121:11684-11689.

Soellner, M.B. et al. (pub. on-line Jun. 2002), "Staudinger ligation of alpha-azido acids retains stereochemistry," J. Org. Chem. 67:4993-4996.

Soellner, M.B. et al. (Oct. 2003), "Site-specific protein immobilization by Staudinger ligation," J. Am. Chem. Soc. 125:11790-11791.

Staudinger, H.; Meyer, J. (1919), "Über neue organische Phosphorverbindunger III. Phosphinmethylenderivate und Phosphinimine," (in German) *Helv. Chim. Acta 2*: 635-646.

Sugama, H. et al. (Jul. 2001), "P-Chirogenic Phosphine/Sulfide Hybrid Ligands," Synthesis, (2001) 2348-2353.

Swinnen, D.; Hilvert D. (Jul. 2000), "Facile, Fmoc-Compatible Solid-Phase Synthesis of Peptide C-Terminal Thioesters," *Org. Lett.* 2:2439-2442.

Tam, J. P.; Yu, Q.; Miao, Z. (pub. on-line Feb. 2000), "Orthogonal Ligation Strategies for Peptide and Protein," *Biopolymers 51*: 311-332.

Tam, J.P. et al (pub. on-line Dec. 2001), "Methods and Strategies of Peptide Ligation," Biopolymers 60:194-204.

Tam, J. P. et al. (1995), "Peptide synthesis using unprotected peptides through orthogonal coupling methods," *Proc. Natl. Acad. Sci. U.S.A. 92*:12485-12489.

Tam, J.P. (1988), "Synthetic peptide vaccine design: Synthesis and properties of a high-density multiple antigenic peptide system," *Proc. Natl. Acad. Sci. U.S.A.* 85:5409-5413.

Tang, Z.; Pelletier, J. C. (1998), "Preparation of amides from acids and resin bound azides: Suppression of intramolecular lactam formation," *Tetrahedron Lett.* 39:4773-4776.

Urpl, F.; Vilarrasa, J. (1986), "New Synthetic 'Tricks.' Advantages of Using Triethylphosphine in Some Phosphorus-Based Reactions," *Tetrahedron Lett.* 27:4623-4624.

Vedejs, E.; Diver, S. T. (1993), "Tributylphosphine: A Remarkable Acylation Catalyst," *J. Am. Chem. Soc. 115*: 3358-3359.

Velasco, M. D. et al. (Jun. 2000), "Isolation, Reactivity and Intramolecular Trapping of Phosphazide Intermediates in the Staudinger Reaction of Tertiary Phosphines with Azides," *Tetrahedron* 56:4079-4084.

von Dohren, H et al. (1997), "Multifunctional Peptide Synthetases," *Chem. Rev.* 97:2675-2705.

Wieland, T. et al. (1953), "Uber Peptidsynthesen. 8. Mitteilung," (In German) *Liebigs Ann. Chem. 583*:129-149.

Wilken, J.; Kent, S. B. H. (1998), "Chemical protein synthesis," *Curr. Opin. Biotechnol.* 9:412-426.

Wilt et al. (1985), "A New synthesis of Peptides from Azides and Unactivated Carboxylic Acids," J. Org. Chem. 50:2601-2603.

Woycechowsky, K. J. et al. (Dec. 1999), "A small-molecule catalyst of protein folding in vitro and in vivo," *Chem.Biol.* 6:871-879.

Zaloom, J.; Roberts, D. C. (1981), "Preparation of Azido Derivatives from Amino Acids and Peptides by Diazo Transfer," *J. Org. Chem. 46*: 5173-5176.

Garcia-Moreno, M.I. et al. (2002), "One-step synthesis of non-anomeric sugar isothiocyanates from sugar azides," Carbohydrate Res. 337:21-23:2329-2334.

Damkaci, F. and DeShong, P. (2002), "Stereoselective Synthesis of α- and β-Glycosylamide Derivatives from Glycopyranosyl Azides via Isoxazoline Intermediates," J. Amer. Chem. Soc. 125(15):4408-4409.

Stimac, A. and Kobe, J. (2000), "Stereoselective synthesis of 1,2-cis- and 2-deoxyglycofuranosyl azides from glycosyl halides," Carbohydrate Res. 329(2):317-324.

Ying, L. and Gervay-Hague, J. (2003), "General methods for the synthesis of glycopyranosyluronic acid azides," Carbohydrate Res. 338(9):835-841.

Pathak, T. (2002), "Azidonucleosides; Synthesis, Reactions and Biological Properties" Chem. Rev. 102(5):1623-1667.

Potts, J. T., Jr. et al. (1963), "Reconstitution of Fully-Active RNase S by Carboxypeptidase-degraded RNase S-Peptide," J. Biol. Chem. 238:2593-2594.

Connelly, P.R. et al. (1990), "Thermodynamics of Protein-Peptide Interactions in the Ribonuclease S System Studied by Titration Calorimetry," Biochemistry 29:6108-6114.

Kelemen, B.R. et al. (1999), "Hypersensitive substrate for ribonucleases," Nucl. Acids Res. 27:3696-3701.

Gregory, M.J. (1967), "Nucleophilic Displacement Reactions at the Thiol Ester Bond. V. Reactions of 2,2,2-Trifluoroethyl Thiolacetate," J. Am. Chem. Soc. 89:2121-2127.

Alper, P.B. et al. (1996), "Metal Catalyzed Diazo Transfer for the Synthesis of Azides from Amines," Tetrahedron Lett. 37:6029-6032.

\* cited by examiner

SEQUENCE LISTING

<160> NUMBER OF SEQ ID NOS: 3

<210> SEQ ID NO 1
<211> LENGTH: 14
<212> TYPE: PRT
<213> ORGANISM: Artificial sequence
<220> FEATURE:
<223> OTHER INFORMATION: Synthetic peptide

<400> SEQUENCE: 1

Glu Thr Ala Ala Ala Lys Phe Glu Arg Gln His Met Asp Ser
1               5                   10

<210> SEQ ID NO 2
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Lysine at position 1 is modified.

<400> SEQUENCE: 2

Lys Glu Thr Ala Ala Ala Lys Phe Glu Arg Gln His Met Asp Ser
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: Synthetic peptide

<400> SEQUENCE: 3

Lys Glu Thr Ala Ala Ala Lys Phe Glu Arg Gln His Met Asp Ser
1               5                   10                  15

METHODS FOR LIGATION OF MOLECULES TO SURFACES

CROSS-REFERENCE TO RELATED APPLICATIONS

This application takes priority under 35 U.S.C. 119(e) from U.S. provisional application 60/499,231 filed Aug. 29, 2003 and is a continuation-in-part of U.S. patent application Ser. No. 10/276,515 which is the U.S. National Stage of PCT application Ser. No. PCT/US01/15440, filed May 11, 2001 now U.S. Pat. No. 6,972,320 and which claims priority under 35 U.S.C. 119(e) to U.S. provisional application 60/203,994, filed May 12, 2000. Each of these applications is incorporated in its entirety by reference herein.

STATEMENT REGARDING GOVERNMENT SUPPORT

This invention was funded in part by the United States government through National Institutes of Health Grant GM44783. The United States government has certain rights in this invention.

BACKGROUND OF THE INVENTION

This invention is in the field of organic chemistry, in particular relating to methods for forming amide bonds useful for the ligation of molecules to surfaces.

Microarrays in which proteins or other compounds are immobilized to a surface enable high-throughput experiments that require only small amounts of analyte. Such protein "chips", for example, can be used to detect protein-ligand, protein-protein, and antibody-antigen interactions. Attaching proteins or other compounds covalently, rather than noncovalently produces more robust surfaces. Attaching compounds to a surface in a uniform rather than random manner and in a manner which results in high-density attachment can provide a substantial advantage in assay sensitivity.

A useful method of forming amide bonds in peptide synthesis is through Staudinger ligation. In the Staudinger reaction a phosphine is used to reduce an azide to an amine:

$$PR_3 + N_3R' + H_2O \rightarrow O{=}PR_3 + H_2NR' + N_2(g).$$

The intermediate in the reaction is an iminophosphorane ($R_3P^+{-}^-NR'$), which has a nucleophilic nitrogen. Villarassa and others have shown that this nitrogen can be acylated, both in intermolecular and intramolecular reactions. (For examples, see: Garcia, J.; Urpí, F.; Vilarrasa, J. *Tetrahedron Lett.* 1984, 25, 4841-4844; Garcia, J.; Vilarrasa, J. *Tetrahedron Lett.* 1986, 27, 639-640; Urpí, F.; Vilarrasa, J. *Tetrahedron Lett.* 1986, 27, 4623-4624; Bosch, I.; Romea, P.; Urpí, F.; Vilarrasa, J. *Tetrahedron Lett.* 1993, 34, 4671-4674; Inazu, T.; Kobayashi, K. Synlett. 1993, 869-870; Molina, P.; Vilaplana, M. J. *Synthesis-Stuttgart* 1994, 1197-1218; Bosch, I.; Urpí, F.; Vilarrasa, J. *J. Chem. Soc., Chem. Commun.* 1995, 91-92; Shalev, D. E.; Chiacchiera, S. M.; Radkowsky, A. E.; Kosower, E. M. *J. Org. Chem.* 1996, 61, 1689-1701; Bosch, I.; Gonzalez, A.; Urpí, F.; Vilarrasa, J. *J. Org. Chem.* 1996, 61, 5638-5643; Maunier, V.; Boullanger, P.; Lafont, D. J. *Carbohydr. Res.* 1997, 16, 231-235; Afonso, C. A. M. *Synthetic Commun.* 1998, 28, 261-276; Tang, Z.; Pelletier, J. C. *Tetrahedron Lett* 1998, 39, 4773-4776; Ariza X.; Urpí, F.; Viladomat, C.; Vilarrasa J. *Tetrahedron Lett.* 1998, 39, 9101-9102; Mizuno, M.; Muramoto, I.; Kobayashi, K.; Yaginuma, H.; Inazu, T. *Synthesis-Stuttgart* 1999, 162-165; Mizuno, M.; Haneda, K.; Iguchi, R.; Muramoto, I.; Kawakami, T.; Aimoto, S.; Yamamoto, K.; Inazu, T. *J. Am. Chem. Soc.* 1999, 121, 284-290; Boullanger P.; Maunier, V.; Lafont, D. *Carbohydr. Res.* 2000, 324, 97-106; Velasco, M. D.; Molina, P.; Fresneda, P. M.; Sanz, M. A. *Tetrahedron* 2000, 56, 40794084; Malkinson, J. P.; Falconer, R. A.; Toth, I. *J. Org. Chem.* 2000, 65, 5249-5252.) Hydrolysis of the resulting amidophosphonium salt gives an amide and phosphine oxide.

Saxon and Bertozzi have shown that the phosphine can also serve as the acyl donor. (Saxon, E.; Bertozzi, C. R. *Science* 2000, 287, 2007-2010; Nilsson, B. L.; Kiessling, L. L.; Raines, R. T. *Org. Left.* 2000, 2,1939-1941) Saxon et al. have reported a modification of the Staudinger ligation to form an amide from an azide using a phosphine reagent. (Saxon, E.; Armstrong, J. I.; Bertozzi, C. R. *Org. Lett.* 2000, 2, 2141-2143.) The phosphine reagents:

when reacted with an azidonucleoside are reported to result in the formation of an amide by acyl group transfer. The ligation is called "traceless" because no portion of the phosphine reagent other than the acyl group remains in the product.

The Staudinger ligation can be used to couple a peptide with no residual atom that remains in the amide product. (See U.S. patent application Ser. No. 10/456,988 filed Jun. 6, 2003, PCT Application PCT/US01/15440 filed May 11, 2001 and published Nov. 22, 2001 as WO 01/87920 A2, Poster presented at the ACS meeting in New Orleans, La. on Mar. 24, 2003 and at the National Organic Symposium in Bloomington, IN on Jun. 1, 2003. See also Nilsson et al. *J Am Chem Soc.* 2003, 125(18), 5268-5269; Soellner et al. *J Org Chem* 2002 67(14), 4993-4996; and Nilsson et al. Org Left. 2001 3(1), 9-12.) A protein, peptide (or fragment thereof) having a C-terminal phosphinothioester reacts with another protein, peptide (or fragment thereof) having a N-terminal azide. The resulting iminophosphorane leads, after an S- to N-acyl shift, to an amidophosphonium salt, where the P—N bond is hydrolyzed spontaneously to produce an amide (See Scheme 1).

SUMMARY OF THE INVENTION

The present invention is a method for a covalent ligation of one or more molecules to one or more surfaces, that is site-specific and both rapid and high yielding. The covalent ligation to the surface is based on the reaction of an azide and a phosphinothioester to form an amide bond as illustrated in Scheme 1. Most generally, either the surface or the molecule to be ligated can be derivatized with a phosphinothioester with the ligating partner (the molecule or the surface, respectively) derivatized with azide group. In a preferred embodiment, the surface is derivatized with a phosphinothioester and the molecule to be ligated to the surface comprises an azide group (as illustrated in Scheme 2).

Molecules that can be immobilized on a surface or substrate in the present invention include, but are not limited to, amino acids, peptides, protein fragments, carbohydrates, lipids, nucleosides or nucleic acids, a reporter molecule, tag or label (e.g., a group whose presence can be detected by optical spectroscopy or mass spectrometry or other instrumental method), including a fluorescent or phosphorescent group, an isotopic label or a radiolabel. Small molecules that can be immobilized on a surface include amino acids, dipeptides, tripeptides, monosaccharides, disaccharides, reporter molecules, haptens that bind selectively to an antibody, ligands that bind to a receptor (such as one or more steroids), drugs or drug candidates, antibiotics and other small molecule therapeutics. Proteins that can be immobilized on a surface can include, among others, enzymes, receptors, antibodies and antibody fragments. Any surface that can be derivatized with phosphinothioester group or an azide group can be employed for ligation of a molecule derivatized with the alternate group. In particular, any molecule that has an azide functional group can be attached to a surface that is derivatized with a phosphinothioester, as long as the molecule and the surface, including surfaces of particulates, are compatible with the chemistry employed.

The phosphinothioester or azide group useful for ligation is typically covalently bound to a surface through a linker group. Linker groups are selected for compatibility with the ligation chemistry and for compatibility with the application of the resulting surface carrying immobilized molecules. The reaction is known to occur in high yield at room temperature in aqueous or wet organic solvents, and is compatible with unprotected functional groups. Further the reaction is "traceless", because no residual atom remains in the amide product formed.

The reaction of this invention allows formation of an amide bond between a wide variety of chemical species. In one embodiment, this invention provides a method and reagents for attaching an amino acid, a peptide, a protein fragment, or a protein to a surface. In general, any amino acid, peptide or protein can be ligated to a surface employing the inventive method. Useful peptides and proteins can be synthetic, semi-synthetic and biosynthetic. In particular, peptides or proteins can be synthesized using solid-phase peptide synthesis or related methods. Peptides and proteins can be isolated from natural sources (e.g., isolated from a bacterial, plant or animal source) or prepared by recombinant methods (e.g., by expression in a recombinant host).

In one embodiment of the present invention, an amino acid, a peptide, protein fragment, containing an azido group reacts with a surface bound phosphinothioester. Where a peptide or protein fragment is used, either terminus of a peptide or protein can be converted to an azide, or the azido group may be on a side chain of an amino acid of the peptide or protein that can be converted to an azide. Analogously, either the amino or acid of an amino acid can be converted to an azide or an azide group may be introduced into the amino acid side chain.

In a specific embodiment, the invention provides a method for covalently attaching one or more proteins to one or more surfaces wherein the immobilized proteins retain 80% or more of the activity of the protein prior to immobilization. Certain proteins immobilized on surfaces employing the methods of this invention can retain greater than 90% of the activity of the protein prior to immobilization. Certain proteins immobilized on surfaces employing the methods of this invention can retain greater than 95% of the activity of the protein prior to immobilization.

In a specific embodiment, the invention provides a method for covalently attaching one or more proteins to one or more surfaces wherein immobilized yields of equal to or greater than 50% are obtained in less than about 1 minute.

In another embodiment, this invention provides a method and reagents for attaching a carbohydrate to a surface. The carbohydrate can be any mono-, di-, tri- or polysaccharide. Carbohydrates can be isolated from natural sources (e.g., isolated from a bacterial, plant or animal source), synthetic or semi-synthetic. More specifically, the carbohydrate is derivatized with an azide group and the surface is derivatized with a phosphinothioester group. Alternatively, the carbohydrate is derivatized with a phosphinothioester group and the surface is derivatized with an azide group.

In another embodiment, this invention provides a method and reagents for attaching a nucleoside, nucleotide or nucleic acid to a surface. The nucleoside or nucleotide can be a ribonucleoside or a ribonucleotide or a deoxyribonulceoside or a deoxyribonucleotide. The nucleic acid can be ribonucleic acid or deoxyribonucleic acid. The nucleic acid may be single-stranded or double stranded. The nucleic acid may be an oligonucleotide, useful for example as a probe. The nucleic acid can be isolated from natural sources (e.g., isolated from a bacterial, plant or animal source), synthetic or semi-synthetic. More specifically, the nucleoside, nucleotide or nucleic acid is derivatized with an azide group and the surface is derivatized with a phosphinothioester group. Alternatively, the nucleoside, nucleotide or nucleic acid is derivatized with a phosphinothioester group and the surface is derivatized with an azide group.

The invention further provides a kit for immobilizing a protein on a surface which comprises a phosphinothiol reagent and a surface to be derivatized with the phosphinothiol reagent. In a specific embodiment the phosphinothiol reagent is diphenylphosphinomethanethiol. The kit can optionally further comprise: one or more additional reagents for initial derivatization of the surface, one or more solvents for use in derivatization, one or more solutions for washing the surface or derivatized the surface, one or more containers for carrying out surface derivatizations; one or more azide reagents for derivatizing molecules to be immobilized on the surface; and/or instructions for carrying out surface derivatization and/or immobilization. The kit may in an alternative embodiment contain one or more prepared surfaces which are derivatized with one or more phosphinothioesters Alternatively the invention provides a kit for carrying out immobilization on a selected surface, for example a glass surface, wherein the kit comprises a phosphinothiol reagent and one or more reagents for carrying out initial derivatization of the surface. In a specific embodiment for carrying out immobilization on a glass surface, a kit of this invention comprises a phosphinothiol reagent, a reagent for initial derivatization of the glass surface with an amine and a reagent for adding a linker group to the glass surface. More specifically, the invention provides a kit which comprises a phosphinothiol reagent, an aminoalkyltrialkoxysilane and an activated ester of PEG (e.g., a disuccinimidyl ester of PEG). The kit can optionally further comprise: one or more additional reagents for initial derivatization of the surface, one or more solvents for use in derivatization, one or more solutions for washing the surface or derivatized the surface, one or more containers for carrying out surface derivatizations; one or more azide reagents for derivatizing molecules to be immobilized on the surface; and/or instructions for carrying out surface derivatization and/or immobilization.

The invention also provides surfaces which are derivatized with one or more phosphinothiolesters for use in immobilization. The invention further provides surfaces to which one or more molecules are immobilized using the methods and reagents of this invention. More specifically, the invention provides surfaces immobilized with one or more proteins (or protein fragments) employing the methods and reagents of this invention. The invention provides surfaces in which the immobilized proteins or protein fragments retain 80% or more of the activity of the free (non-immobilized) proteins or protein fragments.

In a specific embodiment, the ligation method of this invention can be employed to generate a microarray of a plurality of different peptides, proteins, nucleosides, nucleotides, oligonucleotides, saccharides, or small molecules (e.g., drug candidates, haptens).

BRIEF DESCRIPTION OF THE DRAWINGS

FIGS. 1A and B illustrate the yield and activity of immobilization employing the method of this invention. A phosphinothioester-derived slide was spotted for 8 h at room temperature with dilutions (5.64 µM-56.4 µM for ($N_3$)Lys1 S15 ($M_r$, 1773.8), and 4.38 µM-43.8 pM for $N_3$—PEG-S15 ($M_r$, 2284.4)) of an azido-S15 in DMF/$H_2O$ (50:1). The slide was washed thoroughly with DMF, and then with 0.10 M sodium phosphate buffer (pH 7.2). As controls, wild-type S15 (5 µM) was spotted for 8 h, no peptide was spotted, or the slide was treated with $NH_2OH$ before spotting for 8 h with $N_3$-PEG-S15. After incubation with S-protein (10 µg/µL) for 8 h, each spot was assayed for ribonucleolytic activity (FIG. 1B) as described in THE EXAMPLES and fluorescence (FIG. 1A) after staining with a primary antibody (to RNase A) and a secondary antibody conjugated to Alexa Fluor® 488, as described in THE EXAMPLES.

FIG. 3 illustrates the timecourse of immobilization employing the method of this invention. A phosphinothioester-derived slide was spotted with $N_3$—PEG-S15 (5.6 nM) for 1-60 min, and then quenched with $NH_2OH$. After incubation with S-protein (10 µg/µL), each spot was subjected to immunoassay as in FIGS. 1A and B (See THE EXAMPLES).

DETAILED DESCRIPTION OF THE INVENTION

The present invention is based on the used of a modified Staudinger reaction in which an azide reacts with a phosphinothioester to form an amide bond to covalently attach or ligate one or more molecules to a surface. Any azide (a molecule containing an azide group) can be ligated to a phosphinothioester derivatized surface using the methods herein. Any phosphinothioester (a molecule containing a phosphinothioester group) can be ligated to an azide derivatized surface using the methods herein.

A phosphinothioester useful in this ligation can be generated in a number of ways. As illustrated in Scheme 3, an activated carboxylic acid derivative, e.g., a thioester or a N-acylsulfonamide, can be converted into a phosphinothioester. Any method known in the art for forming a phosphinothioester can in general be used. Published POT application PCT/US01/15440 provides an efficient method for generating phosphinothioesters, particularly those of amino acids, peptides and protein fragments using a phosphinothiol reagent. Phosphinothiol reagents can also be employed, as described herein, to provide surfaces derivatized with phosphinothioesters. The phosphinothiol reagent can be used to generate the desire phosphinothioester from activated carboxylic acid derivatives (e.g., thioesters or activated sulfamyl groups) or from a carboxylic acid by conventional coupling reactions mediated by dicyclohexylcarbodiimide or a similar coupling.

A phosphinothioester useful in the ligation reaction of this invention can also be generated from a peptide or protein fragment that is attached to a resin at its C-terminus. For example, a peptide or protein fragment can be released from a resin by reaction with a phosphinothiol reagent of this invention to generate a phosphinothioester. A peptide or protein fragment can be synthesized on an appropriate resin using known methods of solid state peptide synthesis, e.g., Fmoc-based methods. The peptide or protein fragment synthesized on the resin can then be released by reaction with a phosphinothiol to generate a phosphinothioester which then can be ligated with an azide to form an amide bond. In this aspect of the invention, any resin known in the art to be appropriate for peptide synthesis and that is compatible for reaction with a phosphinothiol to generate a phosphinothiol ester can be employed in this invention. Resins known in the art as "safety-catch" resins are of particular interest. See: Backes, B. J.; Ellman, J. A. *J. Org. Chem.* 2000, 64, 2322-2330.

The $R^P$ and $R^B$ moieties (Scheme 3) that can be ligated using the method of this invention can be any of a wide variety of chemical moieties that are compatible with the reaction conditions and which do not undergo undesired reaction with each other or with other functional groups, e.g., in $R_{1-2}$ or X in the phosphinothioester. The X moiety and $R_1$ and $R_2$ groups in Scheme 3 derive from the phosphinothiol reagent and are selected to facilitate the formation of the amide as described below. In this invention one of $R^P$ or $R^B$ comprises a surface to which the other of $R^P$ or $R^B$ is to be covalently linked through an amide bond. The surface can be derivatized with a phosphinothioester ($R^P$) or an azide ($R^B$). In either case, the group active in the ligation is typically indirectly linked to the surface through a linking group. In a preferred embodiment $R^P$ comprises the surface which is a phosphinothioester derivatized surface.

$R^P$ and $R^B$ that do not comprise surfaces, include moieties selected from the group consisting of aliphatic, heteroaliphatic, alicyclic, heteroalicyclic, aromatic, and heteroaromatic any of which can be substituted with one or more halides (particularly F or Cl), OH, OR, COH, COR, COOH, COOR, CONH, CONR or $N(R)_2$ groups where R, independent of other R, is a hydrogen or an aliphatic, heteroaliphatic, alicyclic, heteroalicyclic, aromatic or heteroaromatic group and each R, independently of other R, can be optionally substituted as listed above. In particular, in $R^P$ and/or $R^B$ which contain aliphatic and/or alicyclic portions, one or more non-neighboring $CH_2$ groups can be replaced with O, S, CO, COO, $N(R)_2$ or CONR, where R is as defined above. Any reactive functional group of the $R^P$ or $R^B$ group can be protected from undesired reaction by use of a protecting group (Pr). $R^P$ or $R^B$ can be various carbohydrates, including saccharides, and derivatized saccharides, various amino acids, peptides and proteins, various nucleic acids or components thereof, various lipids and various small molecules, particularly small molecule which form combinatorial libraries, e.g. of drug or other therapeutic candidates. $R^P$ or $R^B$ can also be libraries of peptides, oligonucleotides, nucleic acids, or sugars. Multiple cycles of ligation can be employed to ligate different molecules to the same surface.

In specific embodiments, one of $R^P$ or $R^B$ are amino acids, peptides, or proteins or a plurality of such molecules. The phosphinothioester group may be formed, for example, at the carboxy terminus (C-terminus) of a peptide or protein or at an acid side group of one or more amino acids in a peptide or protein. The azido group may be formed, for example, at the amino terminus (N-terminus) of a peptide or protein or at a basic side group of one or more amino acids in a peptide or protein. The ligation method can be used to ligate two or more amino acids, two or more peptides or two or more proteins (or fragments thereof) to a surface. Multiple cycles of ligation can be employed, for example, to immobilize different peptides, different proteins or protein fragments to a surface. A phosphinothioester group or an azide groups may be covalently linked to a peptide or protein for use in the ligation method herein.

Methods are known in the art for the selective introduction of azide groups into amino acids, peptide or proteins and other molecules to be ligated to surfaces herein. Azide groups can be added to peptide amino groups by conventional reagents and methods. Azides can be added to amino acid side chains by methods that are well-known in the art.

Methods are known in the art for covalent attachment of azide groups to surfaces. For example, surfaces can be initially derivatized with amines, (e.g., alkyl amines) alkyl halides, or esters (particularly activated esters) and these groups can be converted to azides using conventional reagents ($NaN_3$, Triflyl $N_3$).

Phosphinothiols useful in this invention have been extensively described in PCT application Ser. No. PCT/US01/15440, filed May 11, 2001, published as WO 01/87920. Phosphinothiols useful in this invention have the structure:

where:
n and m are 0 or integers equal to 1-3 inclusive and n+m=0-4;
the dashed line indicates that a double bond may be present or that the bond may be part of an aromatic group ($R_4$, $R_6$ and $R_8$ are not present if there is a double bond between the carbons or the bond is a part of an aromatic ring, as indicated);
$R_1$ and $R_2$ are groups independently selected from aliphatic, alicyclic, heteroalicyclic, aromatic, or heteroaromatic groups which are optionally substituted, for example, with halides (particularly F or Cl), OR, COR, COOR, or $N(R)_2$ groups where R, independent of other R, is hydrogen or an aliphatic, alicyclic, heteroalicyclic, aromatic or heteroaromatic group, R is optionally substituted as listed above for $R_1$ and $R_2$; in $R_1$ and $R_2$, one or more non-neighboring $CH_2$ groups can be replaced with O, S, CO, COO, or CONR, and $R_1$ and $R_2$ together can form a ring which includes the P atom and $R_3$—$R_8$, independently, are selected from hydrogens, aliphatic, alicyclic, heteroalicyclic, aromatic or heteroaromatic groups which can be optionally substituted as listed above for $R_1$ and $R_2$, in $R_3$-$R_8$ one or more non-neighboring $CH_2$ groups can be replaced with O, S, CO, COO, or CONR groups where each R, independent of other R are hydrogen, aliphatic, alicyclic or aromatic groups which are optionally substituted as listed above for $R_1$ and $R_2$, and two or more of $R_3$-$R_8$ can be covalently linked to form a cyclic group, including a bicyclic group.

$R_1$ and $R_2$ groups include among others alkyl groups, alkenyl groups, cyclic alkyl, cyclic alkenyl, bicyclic groups, aromatic groups, heteroaromatic group groups, ether groups, ester groups, amide groups, thioether groups, and ketone groups. It is preferred that $R_5$-$R_8$ are not all hydrogens. It is also preferred that n+m is 0, 1 or 2. In specific embodiments, $R_3$ and $R_4$ are both hydrogens and n and m are both zero.

In specific embodiments, the phosphinothiol has the formula:

where $R_1$ and $R_2$ are aromatic or heteroaromatic groups that are optionally substituted as described above and $R_3$ and $R_4$ are as defined above. $R_3$ and $R_4$ are preferably hydrogens. $R_1$ and $R_2$ are preferably electron-withdrawing groups, including phenyl groups and substituted phenyl groups. One of $R_3$ and or $R_4$ and $R_2$ may be covalently linked to form a heteroaromatic ring which may be substituted with groups as listed above. A preferred phosphinothiol reagent is diphenylphosphinomethanethiol. Additional specific phosphinothiol reagents are described in PCT application serial no. PCT/US01/15440, filed May 11, 2001, published as WO 01/87920.

The reactivity of the phosphinothiol reagent can be adjusted by choice of substituents $R_1$ and $R_2$, as is known in the art. In general, these groups are selected to obtain desired reactivity with a selected azide based, at least in part, on the electronic and steric properties of the azide and to minimize sensitivity of the reagent to oxygen. Reagents that are more sensitive to oxygen are, in general, more difficult to handle and require more care in use to avoid undesired levels of oxygen that can destroy or diminish the effectiveness of the reagent. However, ligations with less reactive azide, such as azides of glycosides, can be significantly improved by use of more reactive phosphinothiol reagents. For example, the use of n-alkyl groups, such as n-butyl groups, for $R_1$ and $R_2$ groups can significantly increase reactivity of the reagent.

Additional details for carrying out the ligation method of this invention are found in PCT application serial no. PCT/US01/15440, filed May 11, 2001, published as WO 01/87920.

Additional methods for the synthesis of phosphinothiol reagents are found in published U.S. application 2004/0030105 which is at least in part incorporated by reference herein for the methods provided.

Reactants and reagents employed in the methods of this invention are readily available either from commercial sources or can be prepared using methods that are well-known in the art in view of the description herein. For example, azido glycosides (e.g., azido mannose) and azido nucleosides (e.g., AZT) can be prepared by methods know in the art. The following references (as well as references cited therein) provide exemplary method for generating azide derivatives useful in this invention: Garcia-Moreno M. I. et al. ((2002) Carbohydrate Research 337, 21-23: 2329-2334; Damkaci F. and DeShong P. (2003) J. Amer. Chem. Soc. 125(15):4408-9; Stimac A. and Kobe, J. (2000) Carbohydrate research 329(2):317-324; Ying, L. and Gervay-Hague, J.(2003) Carbohydrate Research 338(9):835-841; Pathak, T. "Azidonucleosides; Synthesis, Reactions and Biological Properties" Chemical Reviews (2002) 102(5): 1623-1668. Azido acids are readily accessible (Zaloom, J.; et al., 1981) and can be used in solid-phase synthesis (Meldal, M.; Juliano, M. A.; Jansson, A. M. Tetrahedron Lett. 1997, 38, 2531-2534).

Thioesters of various biologically interesting molecules are also readily accessible by well-known methods. Phosphinothioesters are prepared by methods illustrated herein or art-known methods and can, in particular, be synthesized by transthioesterification or coupling reactions. Exemplary methods are provided in the examples. Thioesters of various biologically interesting molecules, such as sialic acid or certain lipids, are also readily accessibly by known methods.

Amino acids useful in this invention include the twenty amino acids commonly found in proteins, derivatives of these amino acids (e.g., hydroxyproline, O-phoshoserine, γ-carboxyglutaminate) and rare amino acids (e.g., ornithine, homoarginine, selenocysteine, etc.). Peptides useful in this invention are obtained from any natural source or are prepared synthetically. Peptides include those which exhibit biological function and those which are candidates for exhibiting a biological function. Peptides include libraries of peptide variants in which the individual variants different from one another in amino acid sequence, in sequence length, or derivatization. Proteins and protein fragments useful in this invention are obtained form any natural source, are prepared synthetically or semisynthetically or are prepared by recombinant methods. Proteins include among others glycoproteins, lipoproteins, fusion proteins, enzymes, receptors, antibodies, and antibody fragments. Proteins may be monomers, homodimers, heterodimers, and aggregates containing a plurality of polypeptides. Proteins and protein fragments include libraries of proteins and/or protein fragment variants in which the individual variants different from one another in size or structure, amino acid sequence, or derivatization. Proteins and protein fragment libraries can include libraries containing a plurality of mutant proteins in which one or more amino acids of a polypeptide sequence of the protein or protein fragment are altered from a naturally-occurring (e.g., wild-type) protein sequence.

Nucleosides, nucleotides and nucleic acids useful in this invention are obtained from any natural source, are prepared synthetically or are produced by recombinant methods. Nucleosides, nucleotides include those of adenine, guanine, cytosine, uracil or thymine as well as those of chemical derivatives of these bases e.g. fluorouracil. Nucleic acids and oligonucleotide include those in which the component bases contain adenine, guanine, cytosine, uracil or thymine, as well as those which include one or more component bases which are chemical derivatives of adenine, guanine, cytosine, uracil or thymine. One or more nucleic acids useful herein may be modified as is known in the art to increase their stability. Nucleotides include therapeutic nucleotides. Nucleic acids include RNA and DNA as well as messenger-RNA, transfer-RNA, ribozymes, c-DNA, interfering RNA, structural RNA, cellular or viral genomes or portion thereof. Nucleic acids useful in the invention can be generated by well-known methods of amplification (e.g., PCR). Nucleic acids include those that encode a protein or portion thereof, those that are the complement of a coding sequence or portion thereof, those that include regulatory sequences (e.g., promoter elements, enhancers, etc.), structural nucleic acids. Nucleic acids useful in the invention include those that are ESTs, probes, and primers.

Surfaces that can be used in this invention include, but are not limited to glass (including glass slides), quartz (including optical fibers), various metal surfaces such as gold with thiol monolayers (in particular BIAcore), colloidal gold, semiconductors, diamond, silicon, plastic, ceramics, alum, hydroxyapatite, polyacrylamide, polyimines, polypropylene, latex, rubber, agarose, chitin, chitosan, dextran and derivatized dextrans, cellulose and derivatized cellulose (e.g., nitrocellulose, cellulose acetate), nylon, polyvinyl chloride, and polystyrene (resins, etc), artificial bone material. Surfaces can be flat or curved and can be a film, a plate, a fiber, plate wells, a wafer, a grid, a mesh, a membrane, beads or pins. Surfaces can be rigid or pliable, or the surface of a gel. Surfaces may further be composed of a plurality of solid particles, resins or beads. Surfaces having an immobilized amino acid, peptide, protein fragment, protein, carbohydrate, lipid, nucleoside, nucleotide, nucleic acid, or small molecule attach can be part of an array such as multi-well plates or a microarray on a flat surface. Surfaces which are derivatized, for example to carry amine, OH, epoxy, carboxylate or ester surfaces are commercially available or can be prepared by well-known techniques.

In a specific embodiment of the invention, PEG disuccinimidyl propionate was attached to a glass slide derivatized with 3-aminopropyltriethoxysilane. To generate a surface bound phosphinothioester, phosphinomethanethiol was added to the slide. An azido-peptide was added to the phosphinothioester-derivatized slide and the ligation allowed to proceed, resulting in the peptide being immobilized on the slide through an amide bond. (See Scheme 2)

Methods for generating a phosphinothioester on a surface include but are not limited to reactions between activated esters and phosphinothiols, where the activated ester could be, among others, a hydroxy succinimide ester, pentafluorophenol ester or HOBt ester, carbodiimide coupling, and transthioesterfication using alkyl or aryl thioesters. Phosphines that can be used to generate a phosphinothioester include, but are not limited to, phosphinomethanethiol and ethylene and phenol variants thereof, and phosphines, including imidazole and phenol phosphines disclosed in Saxon, E.: Bertozzi, C. R. Science 2000, 287:2007-2010; and Saxon, E. Armstrong, J. I.; Bertozzi, C. R. Org. Lett. 200, 2: 2141-2143.)

Once a molecule has been immobilized on a surface using the ligation methods of this invention, additional reactions can be performed with the immobilized molecule.

The surfaces carrying immobilized molecules of this invention can be used in a variety of applications including detection and sensing applications, activity or functional screening applications, and isolation, separation and purification applications. The surfaces carrying immobilized molecules of this invention can be used in various diagnostic applications. The surfaces carrying immobilized molecules of this invention can be surfaces of a medical device or implant. In specific embodiments, quartz surfaces and optical fibers are treated to immobilize peptides, proteins, nucleic acids, etc. particularly for detection or sensing application in which analytes bind to or interact with the immobilized molecules. In specific embodiments, surfaces are treated are treated to immobilize peptides, proteins, nucleic acids, carbohydrates or various small molecules (e.g., antigens, haptens or ligands) for applications to isolation, separation or purification of various species which bind selectively to the immobilized molecule. Species which may be detected, isolated, separated or purified using surfaces prepared by the methods herein include among others, proteins, antibodies, antibody fragments, receptors, ligands for receptors, enzyme inhibitors, enzyme activators, antigens, biological cells having certain cell surface features, In specific embodiments, surfaces prepared by the methods herein can be employed in the preparation and functional testing of combinatorial libraries of various small molecules which are drug candidates. In specific embodiments, surfaces prepared by the methods herein can be employed in the preparation and functional testing of libraries of peptides, proteins (protein variants), nucleic acids (nucleic acid variants), and oligonucleotides.

The phosphinothioester or azide group useful for ligation is typically covalently bound to a surface through a linker group. Linker groups are selected for compatibility with the ligation chemistry and for compatibility with the application of the resulting surface carrying immobilized molecules. Linkers include those comprising ether groups, polyethers, alkyl, aryl (e.g., groups containing one or more phenyl rings) or alkenyl groups, ethylene glycol groups. Linkers can range in length from 2 to 1,000 atoms in length. A linker can be based on an alkyl chain in which one or more of the $CH_2$ groups of the chain is replaced with an O, S, NH, CO, or CONH group. A linker can be a substituted alkyl chain in which one or more carbons of the chain carries a non-hydrogen substituent, such as an OH, $NH_2$, or SH group or halide. A linker may be a polymer, such as poly(ethyleneglycol). A linker typically will have one or more functional groups or residue moieties that function for ligation to the linker or that remain after the linker has been ligated to the surface or the molecule to be immobilized.

Details of certain aspects of this invention may also be found in Soellner M. B. et al. Site-Specific Protein Immobilization by Staudinger Ligation (2003) J. Amer. Chem. Soc. (2003) 125:11790-11791.

In a specific embodiment of the present invention, ribonuclease S' (RNase S'), which is a truncated form of RNase S, was used. RNase S' consists of two tightly associated fragments: S-peptide and S-protein. The first 15 residues of S-peptide (S') bind to the S-protein with similar affinity to that of S-peptide (Potts, J. T., Jr.; Young, D. M.; Anfinsen, C. B. J. Biol. Chem. 1963, 238, 2593-2594; Connelly, P. R.; Varadarajan, R.; Sturtevant, J.; Richards, F. M. Biochemistry 1990, 29, 6108-6114) S15 immobilized to a surface through the Staudinger ligation followed by incubation with S-protein resulted in an active RNase S' tethered to the surface.

The S15 peptide was synthesized with an azido group in either the side chain or its main chain. To install an azido group into the side chain, the ε-amino group of Lys1 was replaced with an azido group to generate ($N_3$)Lys1 S15. To install an azido group into the main chain, a PEG fragment with a terminal azido group was attached to the α-amino group of Lys1 to generate $N_3$-PEG-S15.

An amine-derivatized glass slide was treated with an excess of PEG having succinimidyl ester termini followed by diphenylphosphinomethanethiol resulting in a surface-bound phosphinothioester, as illustrated in Scheme 2. It is believed that the PEG layer (Mr) 3,400) prevented the non-specific attachment of protein to the glass surface. Serial dilutions of ($N_3$)Lys1 S15 and ($N_3$)Lys1 S15 were spotted on this phosphinothioester-derivatized slide. The peptide concentrations were 5.64 µM-56.4 pM for ($N_3$)Lys1 S15 and 4.38 µM-43.8 pM for ($N_3$)Lys1 S15. Afterwards, S-protein was spotted on the slide, which was washed with buffer. If S15 was successfully immobilized to the slide through the Staudinger ligation, the S-protein would bind to the immobilized S15 resulting in immobilized RNase S'.

Two types of assays were used to detect the presence of immobilized RNase S'. First, the ribonucleolytic activity of each spot was determined with a fluorogenic substrate. (Kelemen, B. R.; Klink, T. A.; Behlke, M. A.; Eubanks, S. R.; Leland, P. A.; Raines, R. T. Nucleic Acids Res. 1999, 27, 3696-3701). Secondly, immobilized RNase S' was visualized by immunostaining. The assays indicated coupling via a side chain (($N_3$)Lys1 S15) proceeded in 51% yield and had 85% activity. Coupling via the main chain ($N_3$-PEG-S15) proceeded in 67% yield and had 92% activity. These activity values are lower limits because RNAse S' could dissociate to some extent during the timecourse of the assays.

Figure 1A:
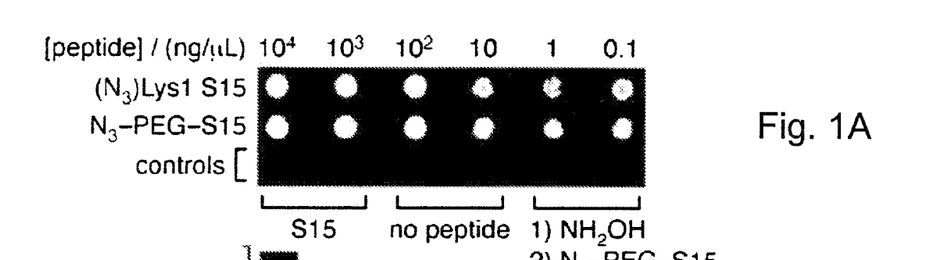
Figure 1B:
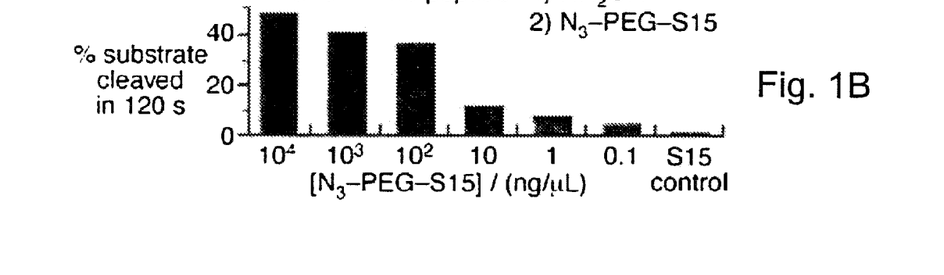

Control experiments indicated that binding occurred only by Staudinger ligation (FIG. 1A, row 3) and that the phosphinothioester does not react with the functional groups of proteinogenic amino acids. S15 without an azido group was spotted on a phosphinothioester-derivatized slide. After incubation of the slide with S-protein, no immobilized peptide was detected with the activity assay or immunoassay. Immobilized peptide was necessary for S-protein to bind to the surface, indicating that the phosphinothioester does not react with the functional groups of proteinogenic amino acids. Azido-peptides did not react with a phosphinothioester-derivatized slide that had been treated with $NH_2OH$, which rapidly cleaves thioesters. (Gregory, M. J.; Bruice. T. C. J. Amer. Chem. Soc. 1967, 89, 2121-2126).

Figure 2:
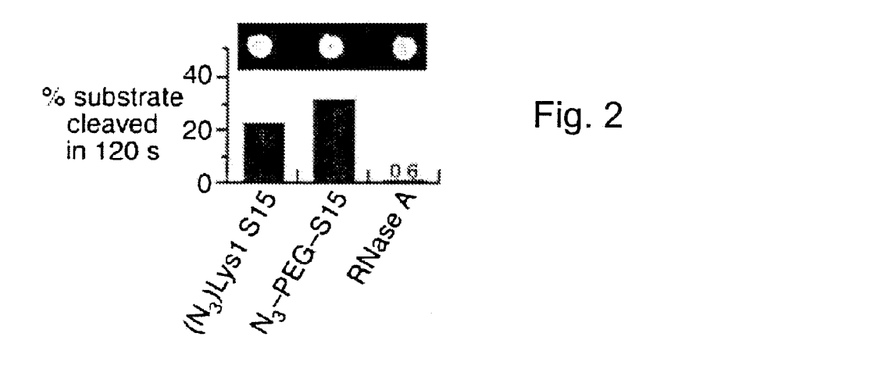
FIG. 2 illustrates the affect of uniform versus random immobilization of protein. A slide displaying NHS-esters was spotted with ribonuclease A (5.0 nM) or phosphinothioester, an azido-S15 (5.0 nM), and S-protein (10 µg/µL). Each spot was assayed as in FIGS. 1A and B (See THE EXAMPLES).

Control experiments also indicate uniform immobilization yield higher results than random immobilization where attachment can occur through functional groups important for activity than does random immobilization. Amine-derivatized slides were treated with NHS-C(O)-PEG-C(O)-NHS in DMF for 2 h, and then with intact RNase A (5.0 nM) in buffer for 8 h. In this case, immobilization will occur randomly via enzymic amino groups. Coupling proceeded in 45% yield (bound peptide: 3.2 fmol/mm$^2$, spotted peptide: 7.0 fmol/mm$^2$), but the coupled RNase A had only 6% activity (FIG. 2). This low activity is likely due to RNase A being attached to the surface through amino groups that are important for function (the side-chain amino groups of Lys7, Lys41 and Lys66 are known to be important for catalysis), which is an intrinsic disadvantage of random immobilization.

Figure 3:
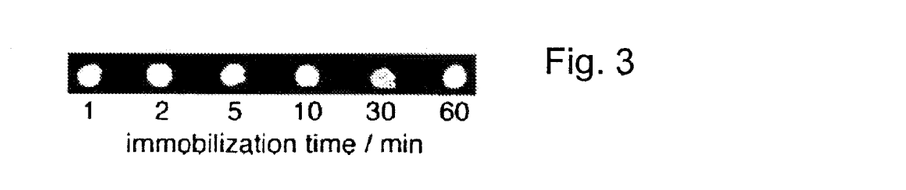

Immobilization by Staudinger ligation of this invention is remarkably rapid. A sub-saturating concentration of $N_3$PEG-S15 was spotted for 1-60 min. After addition of S-protein, an immunoassay showed that the same amount of peptide became attached to the slide in 1 minute as in 1 hour (FIG. 3) or 8 hours (data not shown). Accordingly, the immobilization reaction has $t_{1/2}$<1 min.

The Staudinger ligation is the most efficacious method known for the site-specific, covalent immobilization of a protein. No other approach enables more rapid immobilization or a higher yield of active protein. Starting materials for immobilization, particularly azido-peptides and azido-proteins are readily attainable, and the reactivity of the azido groups is orthogonal to that of biomolecules. Accordingly, the Staudinger ligation of this invention is of great utility in creating microarrays of functional peptides and proteins.

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomers and enantiomer of the compound described individual or in any combination. Specific names of compounds are intended to be exemplary, as it is known that one of ordinary skill in the art can name the same compounds differently. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known in the art including the compounds disclosed in the references disclosed herein are not intended to be included in the claim.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

The invention illustratively described herein suitably may be practiced in the absence of any element or elements, limitation or limitations which is not specifically disclosed herein.

THE EXAMPLES

General Experimental

Chemicals and solvents were from Aldrich with the exception of Fmoc-protected amino acids (Novabiochem). Amine-derivatized slides were from CEL Associates (Arrayt.com). Anhydrous THF, DMF, and $CH_2Cl_2$ were from a CYCLE-TAINER® solvent delivery system (Baker). Other anhydrous solvents were obtained in septum-sealed bottles. Reaction progress was monitored by thin-layer chromatography and visualized by illuminating with UV light or staining with $I_2$. Flash chromatography was performed with silica gel 60, 230-400 mesh (Silicycle). Peptide synthesis was performed using standard Fmoc-protection strategies with HATU activation on an Applied Biosystems Pioneer automated synthesizer. Preparative HPLC was performed with a Varian Dynamax C-18 reversed-phase column. Analytical HPLC was performed with a Vydac C-18 reversed-phase column using a linear gradient of $H_2O$ and $CH_3CN$, both containing TFA (0.1% v/v). NMR spectra were obtained using Bruker AC-300 or Varian UNITY-500 spectrometers. Mass spectra were obtained using electrospray ionization (ESI) or matrix-assisted laser desorption ionization (MALDI) techniques.

Synthesis of Boc-Lys($N_3$)OH

Boc-Lys($N_3$)OH was synthesized from Boc-LysOH by using procedures for Cu(II)-catalyzed diazo-transfer to amines. (Alper, P. B.; Hung, S.-C.; Wong, C.-H. *Tetrahedron Lett.* 1996, 37, 6029-6032.) Boc-LysOH (4.38 g, 17.8 mmol), $CuSO_4 \cdot 5H_2O$ (44.7 mg, 178.2 □mol) and $K_2CO_3$ (3.69 g, 26.8 mmol) were dissolved in $H_2O$ (57 mL) and MeOH (114 mL). $N_3$Tf (triflyl azide, 17.8 mmol in 150 mL $CH_2Cl_2$) was added, and the reaction mixture was stirred overnight. MeOH was removed under reduced pressure. The resulting aqueous solution (50 mL) was diluted with $H_2O$ (0.10 L), and the pH was adjusted to 6.0 with HCl. Sodium phosphate buffer (150 mL, 0.25 M, pH 6.2) was added, and the solution was washed with EtOAc (3×) to remove the triflic amine byproduct. The pH of the washed aqueous layer was adjusted to 2.0 with HCl, and the resulting solution was washed with EtOAc (4×) to extract the desired product. The organic layer was then dried over $MgSO_4$(s) and filtered, and the solvent was removed under reduced pressure to yield Boc-Lys($N_3$)OH as a clear oil (50%). Spectral data. $^1H$ NMR (500 MHz, $CDCl_3$) δ:10.93 (broad s, 1H), 5.11 (d, J=8.3 Hz, 1H), 4.34 (m, 1H), 3.30 (d, J=7.0 Hz, 2H), 1.80 (m, 2H), 1.65 (m, 2H), 1.49 (m, 2H), 1.46 (s, 9H) ppm; $^{13}C$ NMR (125 MHz, $CDCl_3$) δ:179.96, 156.30, 97.44, 55.79, 53.79, 34.66, 31.07, 30.96, 25.20 ppm; MS (ESI) m/z 295.1383 ($MNa^+[C_{11}H_{20}N_4O_4Na]$=295.1382).

Triflyl azide ($N_3$Tf) was prepared as follows. A solution of sodium azide (11.42 g, 175.0 mmol) was dissolved in distilled $H_2O$ (27 mL) with $CH_2Cl_2$ (54 mL) and cooled in an ice bath. Triflyl anhydride (10.0 g, 35.4 mmol) was added slowly over 5 min while stirring continued for 2 h on ice. The mixture was placed in a separatory funnel, and the organic phase was removed. The aqueous portion was extracted with $CH_2Cl_2$ (2×37.5 mL). The organic fractions, which contain the triflyl azide, were pooled, washed once with saturated $Na_2CO_3$(aq), and used without further purification.

Synthesis of ($N_3$)Lys1 S15

SPPS
⇒

Synthesis of $N_3$-PEG-S15

S-Peptide residues 2-15 (SEQ. ID No: 1) was synthesized on a 0.2-mmol scale using pre-loaded Fmoc-Ser-PEG-PS (Applied Biosystems) as the solid support. Boc-Lys(N3)OH (218 mg, 0.8 mmol) was dissolved in DMF (15 mL), and PyBOP (416 mg, 0.8 mmol) was added to the resulting solution. The solution was placed under Ar(g), and DIPEA (206.8 mg, 1.6 mmol) was added. The resulting mixture was added to a peptide synthesis vessel containing S-peptide residues 2-15 on a solid support. The coupling reaction was allowed to proceed for 2 h with mixing via bubbling Ar(g). The resin was then filtered and washed with DMF followed by CH2Cl2. Cleavage cocktail (9.5 mL TFA, 0.5 mL TIS, and 0.5 mL $H_2O$) was then added to the resin. The cleavage reaction was allowed to proceed for 2 h with mixing via bubbling Ar(g). The filtrate was then added dropwise to ice-cold diethyl ether (30 mL), and the deprotected peptide was collected by centrifugation. The pellet was washed (2x) in ice-cold diethyl ether and dissolved in $H_2O/CH_3CN$ (90:10). The peptide (K(N3)ETAAAKFERQHMDS. SEQ. ID NO: 2) was purified by reversed-phase HPLC on a C-18 column. Spectral data. MS (MALDI) m/z 1775.0 ($MH^+$= 1774.8).

S15 (SEQ. ID No: 3) was synthesized on the 0.2-mmol scale using pre-loaded Fmoc-Ser-PEG-PS (Applied Biosystems) as the solid support. $N_3$-PEG-$CO_2$H (444 mg, 0.8 mmol, Novabiochem) was dissolved in 15 mL DMF and PyBOP (416 mg, 0.8 mmol) was added to the resulting solution. The reaction was placed under Ar(g) and DIPEA (206.8 mg, 1.6 mmol) was added. The resulting mixture was added to a peptide synthesis vessel containing S15 on a solid support. The coupling reaction was allowed to proceed for 2 h with mixing via bubbling Ar(g). The resin was then filtered and washed with DMF followed by $CH_2Cl_2$. Cleavage cocktail (9.5 mL TFA, 0.5 mL TIS, and 0.5 mL $H_2O$, premixed) was then added to the resin. The cleavage reaction was allowed to proceed for 2 h with mixing via bubbling Ar(g). The filtrate was then added dropwise to ice-cold diethyl ether (30 mL) and centrifuged to collect the deprotected peptide. The pellet was washed twice in ice-cold diethyl ether and dissolved in $H_2O/CH_3CN$ (90:10). The peptide was purified by reversed-phase HPLC on a C-18 column. Spectral data. MS (MALDI) m/z 2285.8 ($MH^+$=2285.4).

Preparation of Phosphinothioester-Derivatized Surface

PEG ($M_r$ 3400) disuccinimidyl propionate (NHS-C(O)-PEG-C(O)-NHS, Shearwater Polymers, 0.1 M in anhydrous DMF) was added to a glass microscope slide derivatized with 3-aminopropyltriethoxysilane. The reaction was allowed to proceed for 2 h under Ar(g). The reaction mixture was washed extensively with anhydrous DMF. To generate a surface-bound phosphinothioester, phosphinomethanethiol (0.10 M in anhydrous DMF) was added to the slide and allowed to react for 2 h under Ar(g). (Nilsson, B. L.; Kiessling, L. L.; Raines, R. T. *Org. Lett.* 2001, 3, 9-12; Soellner, M. B.; Nilsson, B. L.; Raines, R. T. *J. Org. Chem.* 2002, 67, 4993-4996; Nilsson, B. L.; Honda, R. J.; Soellner, M. B.; Raines, R. T. *J. Am. Chem. Soc.* 2003, 125, 5268-5269) The slide was then washed with anhydrous DMF (20×10 mL) and allowed to dry under a stream of Ar(g).

Staudinger Ligation on Phosphinothioester-Derivatized Surface

An azido-peptide (($N_3$)Lys1 S15 or $N_3$—PEG-S15) in DMF/$H_2O$ (50:1) was added to a phosphinothioester-derivatized slide at a desired concentration. (Peptide concentrations were spotted with a micropipette in 0.8-mm spots. Peptide concentrations ranged from ~5 μM to 50 pM) The Staudinger ligation was allowed to proceed for 8 h in an enclosed chamber saturated with DMF. The slide was then washed with DMF (20×10 mL) and 0.10 M phosphate buffer (pH 7.2, 20×10 mL).

Generation of Immobilized Ribonuclease S'

RNase A and RNase S were removed from commercial S-protein (Sigma Chemical) by reversed-phase HPLC on a Vydac C-4 column. Purified S-protein (10 mg/mL in 0.10 M sodium phosphate buffer, pH 7.2) was incubated for 8 h on a slide presenting immobilized S15. The slide was then washed thoroughly with buffer (30×10 mL). Slides were stored in 0.10 M sodium phosphate buffer, pH 7.2.

Immunoassay of Immobilized Ribonuclease S'

RNase S' attached to the plate was visualized by immunostaining. Rabbit Gig raised against RNase A (Iodizing International) was used at a concentration of 2 μg/mL. Each spot was incubated with primary antibody for 30 min at 23° C. After exposure to primary antibody, the entire slide was washed with PBS (4×20 mL). Secondary antibody conjugated to Alexa Fluor® 488 (Molecular Probes, see Scheme 4) was diluted in PBS to 1 μg/mL and incubated as described for primary antibody. The slide was then washed with PBS (4×20 mL). RNase S' was detected by using a Fluorinate SI fluorescence scanner (Molecular Dynamics). (See FIG. 1A) The quantity of immobilized protein was determined with IMAGEQUANT densitometry software (Molecular Dynamics) and a standard curve generated by spotting various concentrations of Alexa Fluor® 488-conjugated secondary antibody.

Activity Assay of Immobilized Ribonuclease S'

The ribonucleolytic activity of each spot was determined using the fluorogenic substrate, 6-FAM-(dA)rU(dA)$_2$-6-TAMRA (Kelemen, B. R.; Klink, T. A.; Behlke, M. A.; Eubanks, S. R.; Leland, P. A.; Raines, R. T. Nucleic Acids Res. 1999, 27, 3696-3701.) Cleavage of this substrate results in a ca. 200-fold increase in fluorescence intensity (excitation at 494 nm; emission at 515 nm). Assays were performed by adding 0.10 M MES-NaOH buffer (pH 6.0) containing 0.10 M NaCl and 6 μM 6-FAM-(dA)rU(dA)$_2$-6-TAMRA to each spot. At various times, an aliquot was removed from the plate and its fluorescence was recorded. The concentration of RNase S' in each spot was determined by using the equation [RNase S']=(Δ//Δt)/[(I$_f$-I$_0$)(k$_{cat}$/K$_M$)], where Δ//Δt is the initial velocity of the reaction, I$_0$ is the fluorescence intensity prior to exposure to the plate, I$_f$ is the fluorescence intensity after complete hydrolysis of the substrate with excess RNase A, and k$_{cat}$/K$_M$=3.6×10$^7$ M$^{-1}$s$^{-1}$. This value of k$_{cat}$/K$_M$ is for the cleavage of 6-FAM-(dA)rU(dA)$_2$-6-TAMRA by RNase A (Kelemen et al. supra). The catalytic activity of RNase S' is reported to be identical to that of RNase A (Potts, J. T. Jr.; Young, D. M.; Anfinsen, C. B. J. Biol. Chem. 1963, 238, 2593-2594). If the activity of RNase S' were lower than this value, then the actual yield of active enzyme immobilized on the slide would be higher than reported herein.

One of ordinary skill in the art will appreciate that starting materials, reagents, solid substrates, synthetic methods, purification methods, and analytical methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials, additional starting materials, additional reagents, additional methods of synthesis, additional methods of analysis and additional uses of the invention.

SCHEME 1

We claim:

1. A method for immobilizing a molecule on a surface by forming an amide bond which comprises the step of reacting a phosphinothioester with an azide followed by hydrolysis of combined reactants to form an amide bond wherein one of the phosphinothioester or the azide is covalently linked to a surface.

2. The method of claim 1 wherein the azide is covalently linked to a surface.

3. The method of claim 1 wherein the phosphinothioester is covalently linked to a surface.

4. The method of claim 3 wherein the azide is an azide derivatized molecule, and wherein said azide derivatized molecule is an amino acid, peptide, protein or protein fragment.

5. The method of claim 4 wherein the azide derivatized molecule is a protein or a protein fragment and the protein or protein fragment after immobilization retains 80% or more of the activity of the protein or protein fragment prior to immobilization.

6. The method of claim 3 wherein two or more different azides are covalently linked to one surface.

7. The method of claim 6 wherein the two or more different azides are peptides, proteins or protein fragments.

8. The method of claim 3 wherein the phosphinothioester is covalently linked to the surface employing a phosphinothiol reagent.

9. The method of claim 8 wherein the phosphinothiol reagent has the formula wherein $R_1$ and $R_2$, independently, are groups selected from aliphatic, alicyclic, heteroalicyclic, aromatic, or heteroaromatic groups which are optionally substituted with one or more halides, OR, COH, COR, COOH, COOR, or $N(R)_2$ groups where R, independent of other R, is hydrogen or an aliphatic, alicyclic, heteroalicyclic, aromatic or heteroaromatic group and each R can, in turn, be optionally substituted as listed above for $R_1$ and $R_2$; in $R_1$ and $R_2$, one or more non-neighboring $CH_2$ groups can be replaced with O, S, CO, COO, or CONR; and R₃ and R₄, independently, are groups selected from hydrogen, aliphatic, alicyclic, heteroalicyclic, aromatic, or heteroaromatic groups which are optionally substituted with one or more substituents selected from halides, OR, COR, COOR, or N(R)₂ groups, where R, independent of other R, is a hydrogen, an aliphatic group, an alicyclic group, a heteroalicyclic group, an aromatic or heteroaromatic group, and each R is optionally substituted with one or more substituents as listed for R₃ and R₄; and in R₃ and R₄, one or more non-neighboring CH₂ groups can be replaced with O, S, CO, COO, or CONR, wherein R₁ and R₂ are optionally covalently linked to form a cyclic group, or R₃ and R₄ are optionally covalently linked to form a cyclic group.

10. The method of claim 9 wherein in the phosphinothiol reagent, R₃ and R₄ are both hydrogens.

11. The method of claim 10 wherein in the phosphinothiol reagent, R₁ and R₂ are both optionally substituted phenyl groups.

12. The method of claim 11 wherein the phosphinothiol reagent is diphenylphosphinomethanethiol.

13. The method of claim 1 wherein the phosphinothioester is formed employing a phosphinothiol reagent.

14. The method of claim 13 wherein the phosphinothiol reagent is diphenylphosphinomethanethiol.

15. The method of claim 1 wherein the surface is selected from the group of surfaces consisting of a glass surface, a quartz surface, a metal surface, a semiconductor surface, a diamond surface, a silicon surface, a plastic surface, a ceramic surface.

16. The method of claim 1 wherein the surface comprises a plurality of wells in a multi-well plate.

17. The method of claim 1 wherein the surface is a microarray.

18. A kit for immobilizing a protein on a surface which comprises a phosphinothiol reagent and a surface to be derivatized with the phosphinothiol reagent.

19. The kit of claim 18 wherein the phosphinothiol reagent is diphenylphosphinomethanethiol.

20. A kit for immobilizing a protein on a surface, said kit comprising a phosphinothiol reagent, a surface to be derivatized with the phosphinothiol reagent, and one or more reagents for initial derivatization of the surface with a linker.

21. The kit of claim 20 wherein the surface comprises glass and the one or more reagents for initial derivatization of the glass are an aminoalkyltrialkoxysilane and an activated diester of poly(ethyleneglycol).

22. A surface derivatized with a phosphinothiolester.

* * * * *